(12) United States Patent
Lilburn et al.

(10) Patent No.: US 8,677,874 B2
(45) Date of Patent: Mar. 25, 2014

(54) ATRAUMATIC STENT AND METHOD AND APPARATUS FOR MAKING THE SAME

(71) Applicant: Boston Scientific Scimed, Inc., Maple Grove, MN (US)

(72) Inventors: Steve Lilburn, Princeton, MA (US); Paul K. Norton, Lunenburg, MA (US); Michael E. Zupkofska, Rockland, MA (US); Louis Bedard, Leominster, MA (US); Glenn Harding, Sutton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/912,445

(22) Filed: Jun. 7, 2013

(65) Prior Publication Data

US 2013/0269506 A1    Oct. 17, 2013

Related U.S. Application Data

(63) Continuation of application No. 13/441,649, filed on Apr. 6, 2012, now Pat. No. 8,459,164, which is a continuation of application No. 12/630,068, filed on Dec. 3, 2009, now Pat. No. 8,151,682.

(60) Provisional application No. 61/147,307, filed on Jan. 26, 2009.

(51) Int. Cl.
*D04C 1/00* (2006.01)

(52) U.S. Cl.
USPC ..................................... 87/9; 87/34

(58) Field of Classification Search
USPC ................ 87/5, 7, 8, 9, 11, 13, 34; 140/71 R; 623/1.15
See application file for complete search history.

(56) References Cited

U.S. PATENT DOCUMENTS

| | | | | |
|---|---|---|---|---|
| 2,557,816 | A | * | 6/1951 | Di Palma ........................... 87/34 |
| 4,130,046 | A | | 12/1978 | Sokol |
| 4,202,718 | A | | 5/1980 | Mizutani |
| 4,519,290 | A | | 5/1985 | Inman et al. |
| 4,655,771 | A | | 4/1987 | Wallsten |
| 4,893,543 | A | * | 1/1990 | Phillips ............................ 87/34 |
| 5,476,027 | A | | 12/1995 | Uchida |
| 5,501,133 | A | | 3/1996 | Brookstein |
| 5,575,818 | A | | 11/1996 | Pinchuk |
| 5,591,226 | A | | 1/1997 | Trerotola et al. |
| 5,645,559 | A | | 7/1997 | Hachtman et al. |
| 5,800,519 | A | | 9/1998 | Sandock |
| 5,824,077 | A | | 10/1998 | Mayer |

(Continued)

FOREIGN PATENT DOCUMENTS

| | | |
|---|---|---|
| EP | 0150566 | 8/1985 |
| EP | 0423916 | 4/1991 |
| EP | 0775471 | 5/2002 |
| WO | 0061464 | 10/2000 |

OTHER PUBLICATIONS

Pot Search Report and Written Opinion dated Aug. 16, 2012.

*Primary Examiner* — Shaun R Hurley
(74) *Attorney, Agent, or Firm* — Vidas, Arrett & Steinkraus, P.A.

(57) ABSTRACT

A method of braiding a stent includes braiding a number of elongate filaments around a mandrel using tensioned braiding carriers without spooling the filaments to the tensioned braiding carriers to form a braided stent having atraumatic ends.

20 Claims, 10 Drawing Sheets

(56) References Cited

U.S. PATENT DOCUMENTS

| | | |
|---|---|---|
| 6,241,757 B1 | 6/2001 | An et al. |
| 6,520,983 B1 | 2/2003 | Colgan |
| 6,622,604 B1 | 9/2003 | Chouinard et al. |
| 6,626,936 B2 | 9/2003 | Stinson |
| 6,792,979 B2 | 9/2004 | Konya et al. |
| 7,018,401 B1 | 3/2006 | Hyodoh |
| 7,048,014 B2 | 5/2006 | Hyodoh |
| 7,160,323 B2 | 1/2007 | Pulnev |
| 7,311,031 B2 | 12/2007 | McCullagh |
| 8,114,147 B2 * | 2/2012 | Wood et al. .................. 623/1.15 |
| 8,151,682 B2 * | 4/2012 | Lilburn et al. ...................... 87/9 |
| 8,210,084 B2 * | 7/2012 | An .................................. 87/13 |
| 8,459,164 B2 * | 6/2013 | Lilburn et al. .................... 87/34 |
| 2002/0035396 A1 | 3/2002 | Heath |
| 2004/0102855 A1 | 5/2004 | Shank |
| 2005/0049682 A1 | 3/2005 | Leanna |
| 2005/0256563 A1 | 11/2005 | Clerc |
| 2005/0283962 A1 * | 12/2005 | Boudjemline ................. 29/433 |
| 2006/0116752 A1 | 6/2006 | Norton |
| 2007/0119295 A1 | 5/2007 | McCullagh |
| 2008/0167709 A1 * | 7/2008 | An ............................... 623/1.22 |
| 2009/0157158 A1 * | 6/2009 | Ondracek et al. .............. 623/1.2 |
| 2009/0198315 A1 * | 8/2009 | Boudjemline ................. 623/1.2 |
| 2009/0312834 A1 * | 12/2009 | Wood et al. .................. 623/1.44 |
| 2010/0191319 A1 * | 7/2010 | Lilburn et al. ............... 623/1.15 |
| 2012/0150277 A1 * | 6/2012 | Wood et al. .................. 623/1.15 |
| 2012/0186420 A1 * | 7/2012 | Lilburn et al. .................... 87/33 |

* cited by examiner

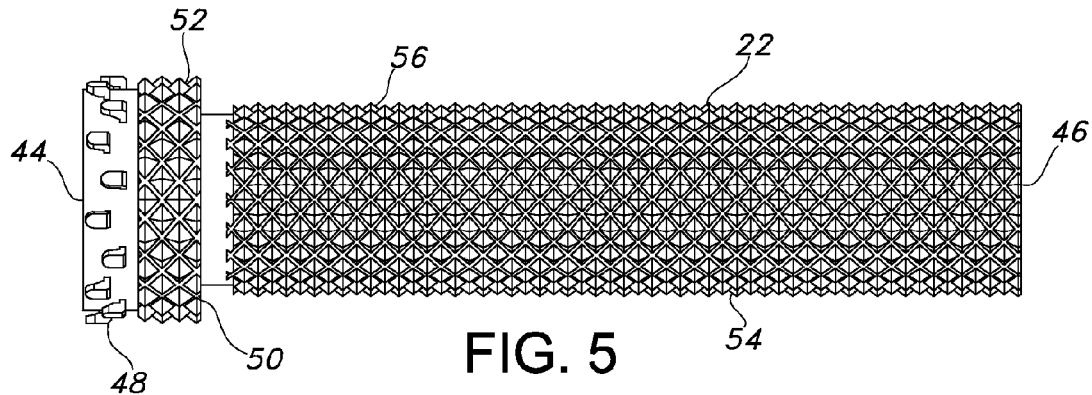
FIG. 5
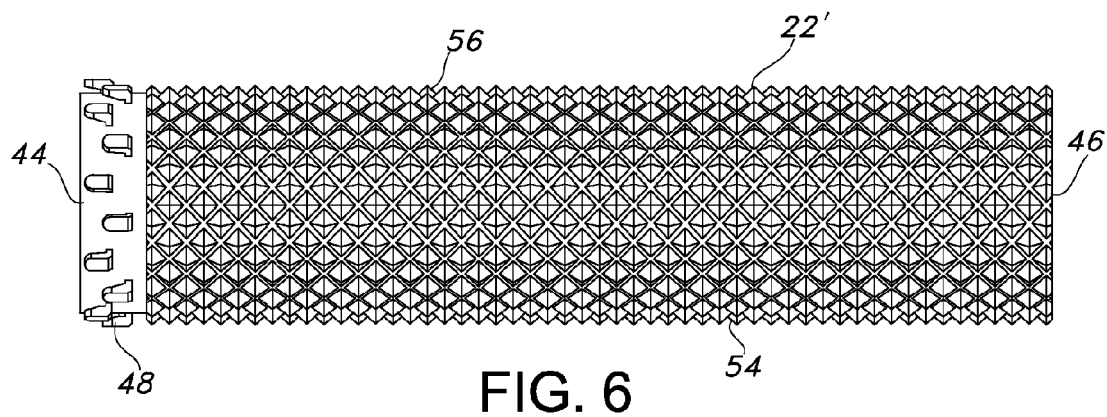
FIG. 6
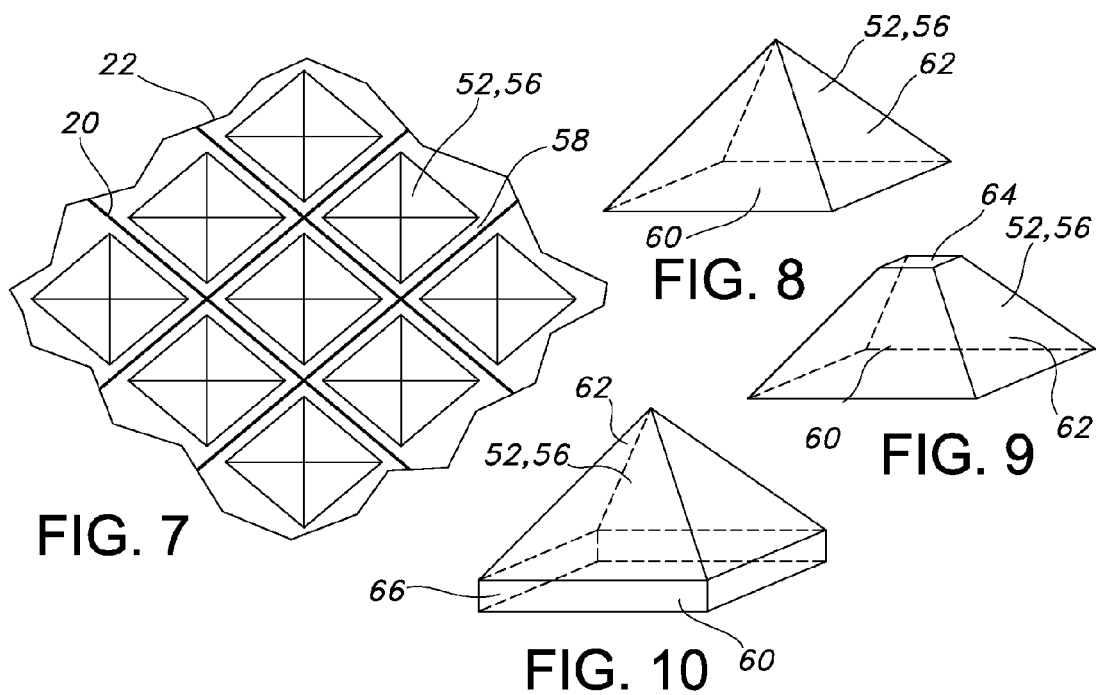
FIG. 7
FIG. 8
FIG. 9
FIG. 10

ATRAUMATIC STENT AND METHOD AND APPARATUS FOR MAKING THE SAME

CROSS-REFERENCE TO RELATED APPLICATIONS

This application is a continuation of U.S. application Ser. No. 13/441,649, filed Apr. 6, 2012, now issued as U.S. Pat. No. 8,459,164, on Jun. 11, 2013, which is a continuation of U.S. application Ser. No. 12/630,068, filed on Dec. 3, 2009, now issued as U.S. Pat. No. 8,151,682, which claims priority to U.S. Provisional Application No. 61/147,307, filed Jan. 26, 2009, the content of each incorporated herein by reference.

FIELD OF THE INVENTION

The present invention is related to an atraumatic stent and methods, apparatus and systems for making the same. More particularly, the present invention is related to an atraumatic braided stent and braiding methods, braiding mandrels and braiding machines for making the same.

BACKGROUND OF THE INVENTION

Braided stents have typically been braided on a smooth mandrel. The ends of the braiding wires were typically gathered beyond an end of a braiding mandrel, and the wires where then secured, typically by tying or taping, to the mandrel end portion, after which braiding, either by hand or machine, commenced.

The braiding angle was controlled by the angle at which the stent wires were disposed over the mandrel. Many stents, however, use metallic wires which may shift or move during braiding as a result of forces imparted on the wires during the braiding. This may result in a variation of the braiding angle though the stent, in particular for stents braided with varied diameters, such as flared, flanged and/or tapered stents. Variation in the braiding angle may result in undesirable variation of radial expansion or compression forces or deployment forces of the so formed stent. Such variations may also effect the consistency of the size of the openings, e.g., cell size, across the stent.

Wire used in the fabrication of the stent is generally fed from a spool onto the mandrel. In this manner, multiple stents could be formed by feeding enough material to the mandrel during the braiding process and thereafter cutting the resulting long stent into multiple smaller stents. After braiding the long stent, the wire portions gathered beyond the mandrel end were trimmed. The trimming of such excess wire needlessly wastes material. As many early stents were braided simply with stainless steel wires, the cost of discarding this excess wire material was minimal. More recently, however, stent wires of more expensive materials, such as nitinol or composite nitinol have been used. The cost of the discarded material has become much more costly.

Thus, there is a need in the art to provide a method for braiding a stent where material costs are minimized and where variations in the stent configuration, including braiding angle, are also minimized. Further, there is a need in the art to provide a method for braiding a stent with atraumatic ends from discrete wire lengths so that the braiding angle(s) of the stent and the size and orientation of the atraumatic ends are controllably provided to produce atraumatic stents with consistency while allowing for mass production of the atraumatic stents. Moreover, there is a need optimize stent manufacturing to more tightly control stent specifications, including optimizing material control and including ability to create any specific quantity of custom stents as desired.

SUMMARY OF THE INVENTION

The present invention provides braiding methods, braiding mandrels, braiding machines and braided stents which avoid and solve the undesirable concerns of the prior art. The braided stents of the present invention have a substantially controlled braiding angle, including a substantially constant braiding angle, if desired, throughout its longitudinal expanse, including portions having varied diameters, such as tapered portions, flared portions and/or flanged portions. For example, a substantially constant braiding angle, for example but not limited to 110°, may be desired throughout the longitudinal expanse of a stent, including portions having varied diameters. Additionally, the braided stents of the present invention may have varied diameter portions where the braiding angle is controllably different in one varied diameter portion as compared to another varied diameter portion and/or is controllably different in one or more varied diameter portions as compared to the longitudinal expanse of the stent. Further, the controlled braiding angle of the inventive stent may vary from one angle, for example but not limited to 90°, at one end, to a different angle, for example but not limited to 120°, at an opposed second end where not only the end angles but also all of the transition angles between the opposed ends are controlled. Such inventive stents are produced by methods and devices of the present invention which include, inter alia, braiding mandrels having specifically designed grooves and projections and constant force braiding carriers for tangentially delivering stent filaments for braiding the filaments onto such specifically designed mandrels.

In one embodiment of the present invention, a method of braiding a stent is provided. The method may include the steps of (a) providing a number of elongate filaments, each of the filaments having opposed ends and an intermediate portion between the opposed ends; (b) providing a number of tensioned braiding carriers; (c) providing a braiding mandrel having opposed proximal and distal ends, the braiding mandrel comprising a number of circumferentially spaced-apart securement projections at the distal end of the braiding mandrel; (d) securably disposing the intermediate portion of one of the filaments to one of the securement projections; (e) securing one of the opposed ends of the one filament to one of the tensioned braiding carriers without spooling the one filament to the one constant force braiding carrier; (f) securing the other opposed end of the one filament to a different second tensioned braiding carrier without spooling the one filament to the second tensioned braiding carrier; (g) repeating steps (d) through (f) until all of the intermediate portions of the filaments are securably disposed to different ones of the securement projections and until each end of the number of filaments are secured to a different one of the tensioned braiding carriers; (h) moving the constant force carriers around the mandrel, for example in a generally circular and serpentine motion; and (i) longitudinally advancing the mandrel in a direction substantially perpendicular to the motion of the constant force carriers to braid the filaments to form a braided stent. Advancing the mandrel may include moving the mandrel with respect to the perpendicular motion of the tensioned braiding carriers, moving the tensioned braiding carriers longitudinally with respect to the mandrel, and combinations thereof. The tensioned braiding carriers each may include a retractable carrier filament for releasably securing a stent filament thereto. The tensioned braiding carriers each may also include a wheel around which the retractable carrier filament may be coiled.

In another embodiment of the present invention, a method for braiding a stent comprises the steps of (a) providing a number of elongate filaments, each of the filaments having opposed ends and an intermediate portion between the opposed ends; (b) providing a number of braiding carriers; (c) providing a braiding mandrel having opposed proximal and distal ends, the braiding mandrel comprising a number of circumferentially spaced-apart securement projections at the distal end, the mandrel further comprising a plurality of grooves; (d) securably disposing the intermediate portion of one of the filaments to one of the securement projections at the distal end of the mandrel; (e) securing one of the opposed ends of the one filament to one of the braiding carriers; (f) securing the other opposed end of the one filament to a different second braiding carrier; (g) repeating steps (d) through (f) until all of the intermediate portions of the filaments are securably disposed to different ones of the securement projections and until each end of the number of filaments are secured to a different one of the braiding carriers; (h) moving the braiding carriers around the mandrel, for example in a generally circular and serpentine motion; (i) longitudinally advancing the mandrel relative to a direction substantially perpendicular to the motion of the braiding carriers to braid the filaments to form a braided stent; and (j) applying a constant tension force from the braiding barriers to the filaments during the braiding steps (h) through (i).

In yet another embodiment of the present invention, a method for braiding a stent comprises the steps of (a) providing a number of elongate filaments, each of the filaments having opposed ends and an intermediate portion between the opposed ends; (b) providing a number of tensioned braiding carriers; (c) providing a braiding mandrel having opposed proximal and distal ends, the braiding mandrel comprising a number of circumferentially spaced-apart securement projections at the distal end, the braiding mandrel further comprising a plurality of grooves; (d) securably disposing the intermediate portion of one of the filaments to one of the securement projections at the distal end of the braiding mandrel; (e) securing one of the opposed ends of the one filament to one of the tensioned braiding carriers without spooling the one filament to the one tensioned braiding carrier; (f) securing the other opposed end of the one filament to a different second tensioned carrier without spooling the one filament to the second tensioned carrier; (g) repeating steps (d) through (f) until all of the intermediate portions of the filaments are securably disposed to different ones of the securement projections and until each end of the number of filaments are secured to a different one of the tensioned carriers; (h) moving the tensioned carriers around the mandrel, for example in a generally circular and serpentine motion; and (i) longitudinally advancing the mandrel relative to a direction substantially perpendicular to the motion of the tensioned carriers to braid the filaments by tangentially disposing the filaments into the grooves to braid the filaments to form a braided stent.

In a still further embodiment of the present invention, a braided stent is provided. The braided stent comprises a plurality of elongate filaments inter-braided to form a tubular well structure, the filaments being inter-braided at a braiding angle formed at crossing filament locations; the tubular wall structure comprising a first portion having a first diameter, a second portion having a second diameter which is different from the second diameter and a transition portion disposed between the first portion and the second portion; wherein the braiding angles in the first portion, the second portion and the transition portion are substantially equal. Alternatively, the braiding angles of these portions may be different, but nevertheless controlled. Moreover, the stents of the present invention are not limited to those having a varied diameter and/or flared or flanged portions. A constant diameter or substantially constant diameter may also be provided. Such a constant or substantially constant diameter stent may have improved tolerances, i.e., fewer variations, of cell configuration, for example braiding angles, cell size and the like.

Further, a braiding mandrel for braiding the tubular stent of the present invention desirably comprises an elongate tubular member having opposed proximal and distal ends; securement projections circumferentially disposed at spaced-apart locations at the distal end for engaging a filament from a braiding machine; a plurality of annular or annular disposed grooves along the longitudinal length of the member. The grooves may extend at an angle from about 5° to about 85° from a longitudinal axis of the member.

Use of the optimized braiding techniques and braiding components of the present invention allow a manufacturer to make a customized stent. Such a customized stent may be specific to any one set of specifications, including but not limited to braiding angle, stent diameter, stent length, stent shape and then like. Moreover, such customized stents may be produced with optimized manufacturing techniques, thereby providing customized stents with improved quality control as compared to the prior art.

These and other features and advantages of the present invention will become apparent from the following detailed description of illustrative embodiments thereof, which is to be read in connection with the accompanying drawings.

BRIEF DESCRIPTION OF THE DRAWINGS

FIG. 5 is a side elevational view of the braiding mandrel of the present invention.

FIG. 6 depicts a braiding mandrel having a substantially constant diameter according to the present invention.

FIG. 7 is an exploded view of a portion of the mandrel of FIG. 5 depicting the raised mandrel projections.

FIGS. 8-10 depict details of the raised mandrel projections of FIG. 7.

DETAILED DESCRIPTION OF THE PREFERRED EMBODIMENTS

Figure 1:
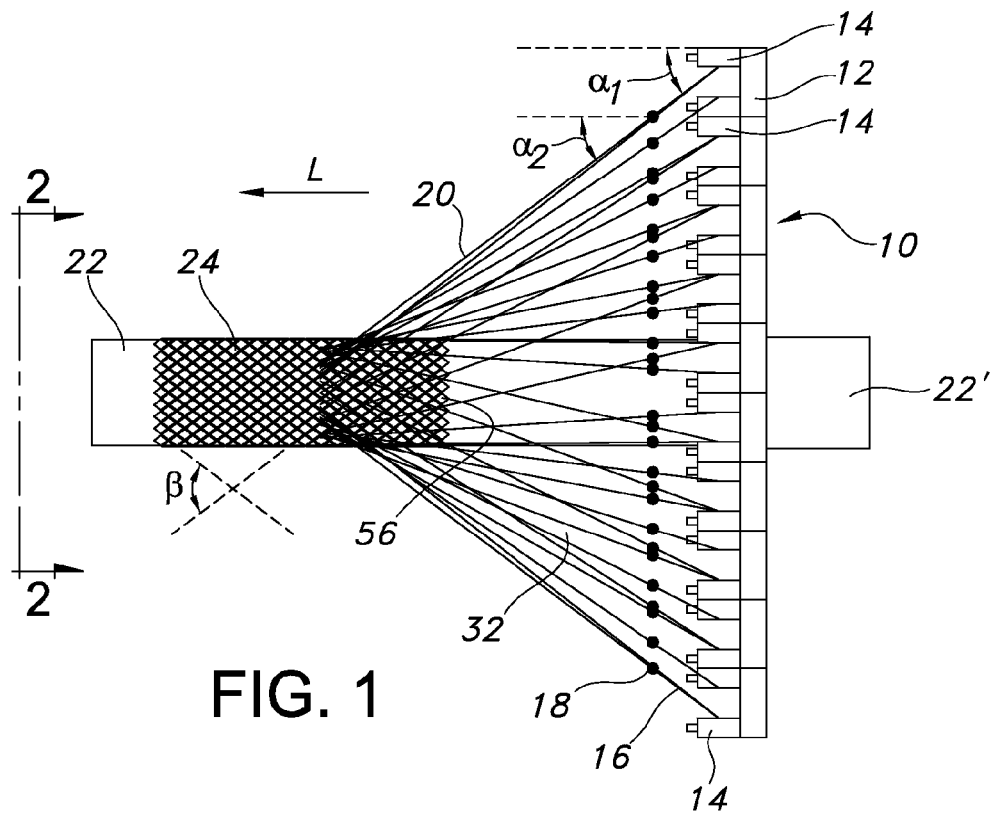
FIG. 1 is a side elevational schematic view of braiding machine of the present invention.

FIG. 1 is a side elevational schematic view of braiding machine 10 of the present invention. Certain features of the braiding machine 10, such as motors, controls, safety features, etc., are not shown for simplicity. The braiding machine 10 of the present invention, however, may suitably include such features without limitation. Braiding machine 10 includes a number of notch gears 12. Each notch gear 12 may include a one or more, typically a pair of, tensioned or constant force braiding carriers 14 disposed thereon. The tensioned or constant force braiding carriers 14 have a retractable carrier filament 16. The retractable carrier filament 16 is releasably secured to a stent-forming filament 20 via a clip 18. The stent-forming filaments 20 are braided over a mandrel 22 to form a stent 24 of the present invention.

Figure 2:
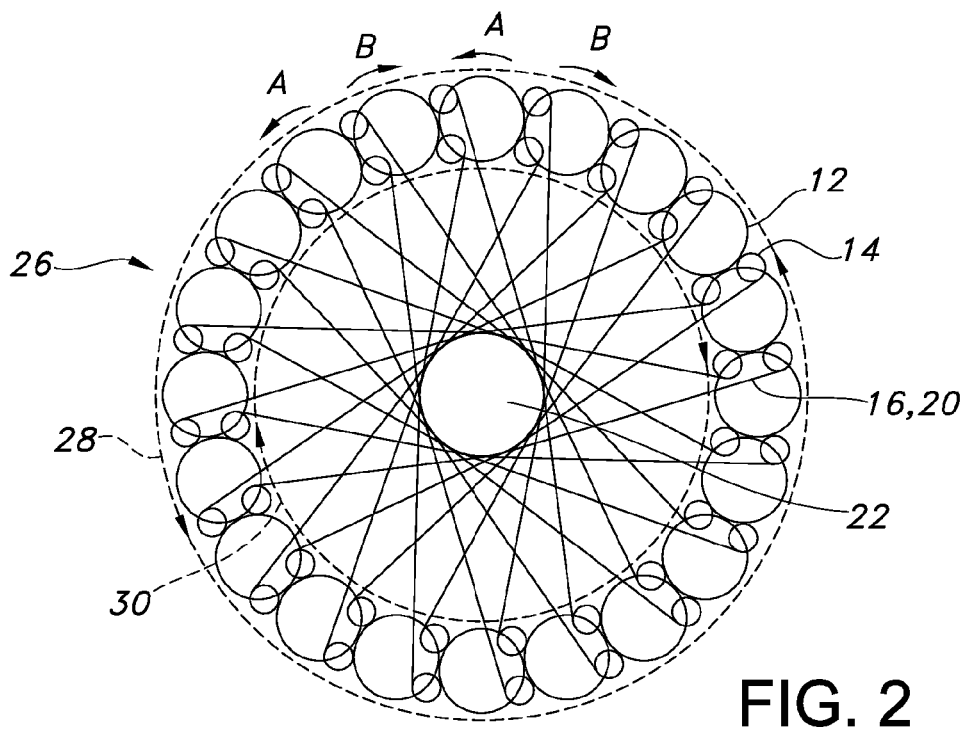
FIG. 2 is a front view of the braiding machine of FIG. 1 taken along the 2-2 axis.

The stent-forming filaments 20 are braided typically in a one-over and one-under pattern to form a braided tubular structure, i.e., stent 24. Other braiding arrangements are possible, including but not limited to those depicted in FIGS. 4C and 4D. The braiding operation is schematically depicted in FIG. 2, which is a front view of the braiding machine 10 of FIG. 1 taken along the 2-2 axis. Note that as used herein the term braiding includes weaving and the like. FIG. 2 depicts the braiding machine 10 as having twenty notch gears 12 arranged in a generally circular configuration 26. The number of notch gears 12 used with the braiding machine 10 is not limited to twenty and any suitable number of notch gears 12 may be used. Each notch gear 12 is adapted to rotate in the opposite direction as its neighboring notch gear 12, as illustrated by arrows A and B in FIG. 2. This counter-rotation movement of the notch gears 12 passes the braiding carriers 14 in a sinusoidal fashion from one notch gear 12 to an adjacent or juxtaposed notch gear 12, thus causing the carriers 14 to revolve, or move in a circumferential manner, about a longitudinal axis L on which the circle of notch gears 12 is desirably centered. The circular configuration 26 of the notch gears 12 and carriers 14 achieve a generally circular but sinusoidal movement of the carriers 14 to braid the filaments 20 over the mandrel 22 in a one-over and one-under fashion to form the stent 24.

Figure 3:
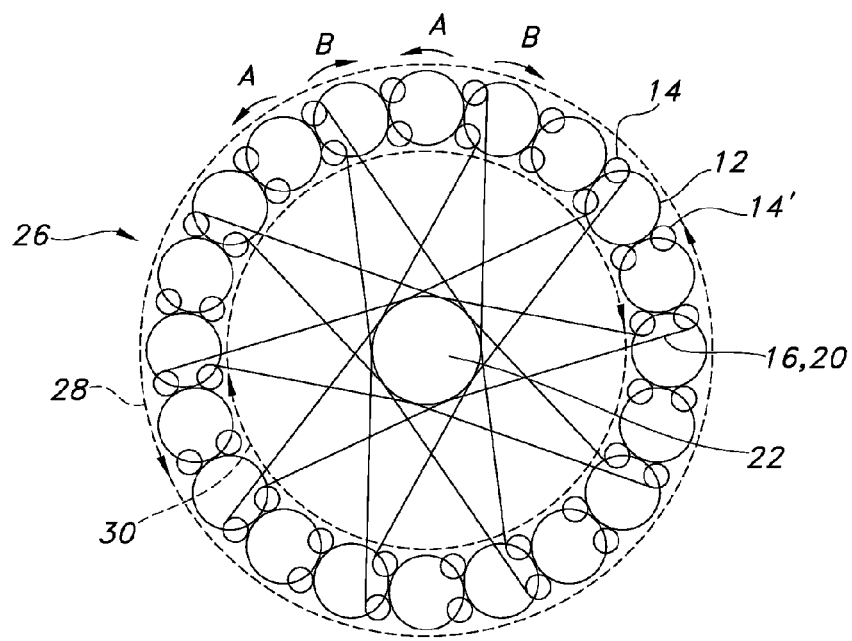
FIG. 3 is an alternate embodiment of the braiding machine of FIG. 2.

As depicted in FIG. 3, not every carrier 14 need have a filament 16, 20 disposed there with. For example, carriers 14' may not have a filament 16, 20 while carriers 14 may have the filaments 16, 20. In such a manner, the number of filaments 20 making the stent 24 may be altered while using the same braiding machine 10.

During braiding, the mandrel 22, around which braided stent 24 is formed, is moved in a controlled manner substantially along a longitudinal axis L about which the circle 26 of notch gears 12 is centered and about which the carriers 14 revolve. FIG. 1 illustrates, from the side, such a configuration. During braiding, filaments 20 extend from the braiding machine 10 to the mandrel 22 in a generally conical configuration, as shown in FIG. 1. The present invention, however, is not so limited. For example, as an alternative or in addition to, the mandrel may stay fixed in place and the braiding or weaving machine may be moved the length of the mandrel.

As illustrated in FIG. 2, as two carriers 14 cross one another along their generally circular but sinusoidal movement, their respective filaments 20 form an overlap such that the filament 20 associated with a carrier 14 on the outer radius 28 of the circle 26 of the notch gears 12 is disposed radially outward (with respect to the axis of the stent being assembled) relative to the filament 20 associated with a carrier 14 on the inner radius 30 of the circle 26 of notch gears 12. The carriers 14 depicted toward the outer radius 28 of the circle 26 of notch gears 12 move in a generally counterclockwise direction, and the carriers 14 disposed toward the inner radius 30 of the circle 26 of notch gears 12 move in a generally clockwise direction.

The space contained within the cone formed by the filaments 16, 18 extending between the carriers 14 and the mandrel 22 and including the space occupied by the mandrel 22 is referred to herein as the "braiding zone" 32, as depicted in FIG. 1. Although the angles $\alpha_1$ and $\alpha_2$ of the filament 16, 20 to the mandrel 22 may be varied as desired, $\alpha 1$ and $\alpha 2$ preferably each comprise an angle of approximately 55° when the braiding angle of a braided stent $\beta$ is approximately 110°. These angles may vary dependent upon, inter alia, the exact radial position of the carriers 14 relative to the mandrel 22. Further, these angles are nonlimiting and any suitable braiding angle $\beta$, including acute or obtuse braiding angle $\beta$. For example, the braiding angle $\beta$ may vary from about 10° to about 170°, desirably from about 30° to about 150°, preferably from about 100° to about 120°. As used herein, the phrase "substantially along the longitudinal axis" as used with respect to the alignment of the moving mandrel means that the mandrel does not have to be perfectly centered in the braiding zone, but merely needs to be aligned close enough to the longitudinal axis L such that the angles of the filaments between the mandrel and the carriers allows the braiding operation to create a functional braid without tangling the filaments.

Figure 4A:
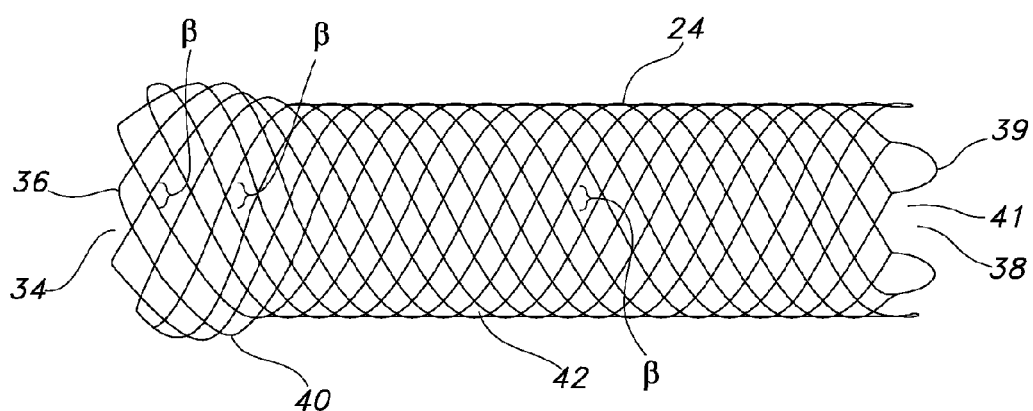
FIG. 4A depicts a stent according to the present invention.

FIG. 4A depicts a stent 24 according to the present invention. The stent 24 may include a first atraumatic end 34 and an opposed second atraumatic end 38. The first atraumatic end may be formed by bending the filaments 20 at or about the middle portion of the length of the filaments 20 to form bends 36 thereat. The second opposed atraumatic end 38 may be formed by bending the filaments 20 into closed loops 39. The filaments 20 forming the closed loops 39 may be secured to one and the other by welds 41. The stent 24 of the present invention is not limited to the use of welds 41 to join stent filaments 20, and other mechanical means, such as the use of hypotubes, twisting or tying of the filaments and the like, may suitably be used. The stent 24 of the present invention may also include one or more outwardly flared or flanged portions 40. In such a case, the diameter of the flared portion 40 is greater than the diameter of the longitudinal expanse portion 42 of the stent 24. The longitudinal expanse portion 42 of the stent 24 may be a constant diameter, including a substantially constant diameter. Such stent configurations are non-limiting, and other stent configurations may be achieved with the systems, devices and methods of the present invention. For example, the stent 24 may include outwardly flared portions at both ends 34, 38, may have a tapered configuration in place of or in conjunction with the longitudinal expanse portion 42 of the stent 24.

Further, the braiding angle β throughout the stent 24, including the flanged portion 40 and the longitudinal expanse portion 42, is substantially constant. For example, as depicted in FIG. 4A, the braiding angle β is about 110°±3°, desirably about 110°±1°. Stents of the prior art typically have a variation of ±10° or greater in stent transitional regions, such as the flared or flanged portions of their stents. Such variations, however, present undesirable variability in stent performance, such as radial expansion force, radial compression force or deployment force. The present invention avoids such undesirable variations through the use of, inter alia, the tensioned or constant force braiding carriers 14 (described in further detail below in conjunction with the description of FIG. 22), the constant force bobbin carriers 110 (described in further detail below in conjunction with the description of FIG. 24), the braiding mandrel 22 having raised projections 52, 56, (optionally) 70 (described in further detail below in conjunction with the description of FIGS. 5-16B), and/or stent-filament-holding securement projections 48 on the mandrel 22 (described in further detail below in conjunction with the description of FIGS. 6, 14 and 15).

Figure 4B:
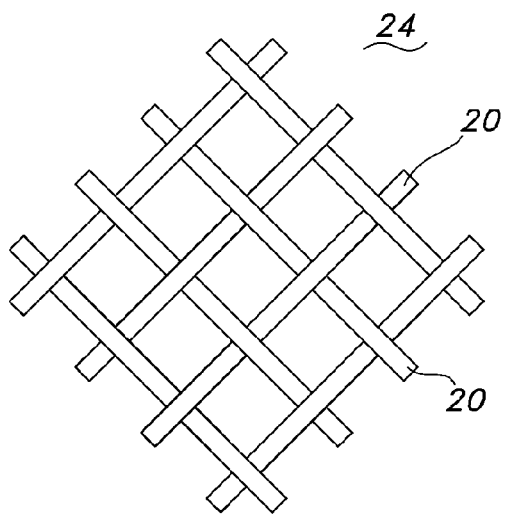
FIG. 4B is an exploded view of the stent of FIG. 4A illustrating a one-under and one-over braiding configuration.
Figure 4C:
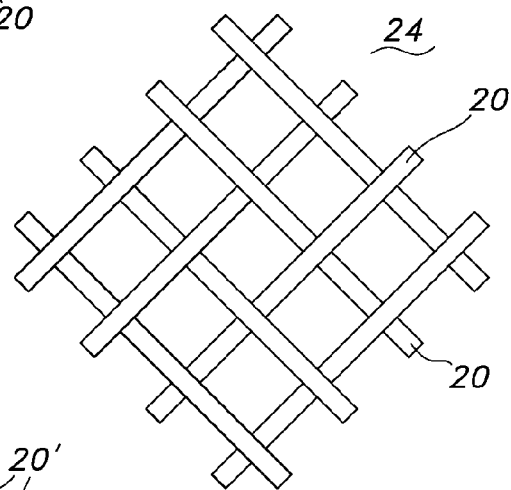
FIG. 4C is an exploded view of the stent of FIG. 4A illustrating a two-under and two-over braiding configuration.
Figure 4D:
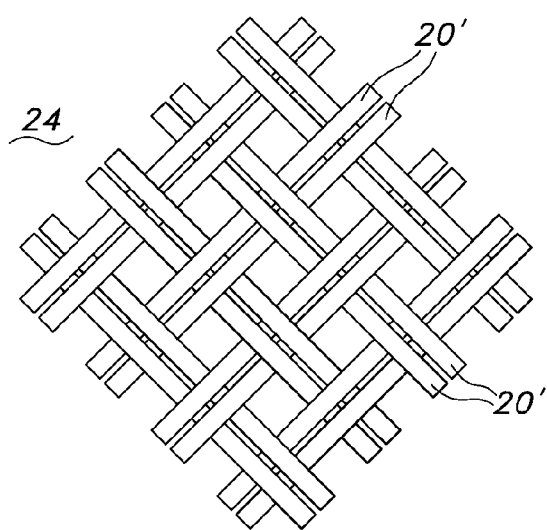
FIG. 4D is an exploded view of the stent of FIG. 4A illustrating a pair of filaments in a one-under and one-over braiding configuration.

The one-under and one-over braiding configuration of the stent 24 of FIG. 4A is depicted in an exploded view in FIG. 4B. As depicted in FIG. 4B, the filaments 20 alternate in a braiding pattern having a 1/1 intersection, i.e., one-under and one-over pattern. The stent 24, however, is not so limited. As depicted in FIG. 4C, stent 24 may include the filaments 20 braided in a two-under and a two-over pattern. Other braiding patterns known in the art may also be suitably be used. Further, as illustrated in FIG. 4D, stent 24 may be braided by using a pair of filaments 20' in a one-under and one-over pattern. The filaments 20' may be the same or may be different, i.e., may have the same or different dimensions, shapes and/or materials of construction. Moreover, the filaments 20' may suitably be braided in other braided patterns, such as but not limited to, for example, the two-under and two-over pattern. Desirably, the braided filaments 20, 20' non-interlockingly engage one and the other in the braided pattern. Such non-interlocking braiding pattern excludes, if desired, inter-twisting, inter-looping, inter-engaging and the like at the intersection of the braided filaments 20, 20'. If desired, the braided or woven filaments 20, 20' may be braided or woven in an interlocking manner.

Desirably, the filaments 20 are made from any suitable implantable material, including without limitation nitinol, stainless steel, cobalt-based alloy such as Elgiloy®, platinum, gold, titanium, tantalum, niobium, polymeric materials and combinations thereof. Useful polymeric materials may include, for example, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, natural silk, polyvinyl chloride, polytetrafluoroethylene, including expanded polytetrafluoroethylene (ePTFE), fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, and copolymers and combinations thereof. Further, useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), polyphosphate ester) and the like. Wires made from polymeric materials may also include radiopaque materials, such as metallic-based powders, particulates or pastes which may be incorporated into the polymeric material. For example the radiopaque material may be blended with the polymer composition from which the polymeric wire is formed, and subsequently fashioned into the stent as described herein. Alternatively, the radiopaque material may be applied to the surface of the metal or polymer stent. In either embodiment, various radiopaque materials and their salts and derivatives may be used including, without limitation, bismuth, barium and its salts such as barium sulphate, tantalaum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent may be selectively made radiopaque at desired areas along the wire or made be fully radiopaque, depending on the desired end-product and application. Further, the filaments 20 have an inner core of tantalum, gold, platinum, iridium or combination of thereof and an outer member or layer of nitinol to provide a composite wire for improved radiocapicity or visibility. Desirably, the inner core is platinum and the outer layer is nitinol. More desirably, the inner core of platinum represents about at least 10% of the wire based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Patent Application Publication 2002/0035396 A1, the contents of which is incorporated herein by reference. Preferably, the filaments 20 are made from nitinol, or a composite wire having a central core of platinum and an outer layer of nitinol.

FIG. 5 is a side elevational view of a braiding mandrel 22 according to the present invention. The braiding mandrel 22 is a tubular, typically metal such as stainless steel, cylindrical member having a distal end 44 (distal from the circle 26 of notch gears 12 when disposed on the braiding machine 10) and an opposed proximal end 46 (proximal to the circle 26 of notch gears 12 when disposed on the braiding machine 10). The distal end 44 includes securement projections 48, which, as described below, are useful for engaging the stent filaments 20 prior to the commencement of braiding. The distal end 44 further includes a distal portion 50 which has a larger diameter than the longitudinal portion 54 of the mandrel 22. After braiding the filaments 20, the distal mandrel portion 50 forms the flared stent portion 40, and the longitudinal mandrel portion 54 forms the longitudinal expanse stent portion 42. Both the distal mandrel portion 50 and the longitudinal mandrel portion 54 may include raised mandrel projections 52 and 56, respectively. As described below, the raised mandrel projections 52, 56 are useful for forming guides for receiving the filaments 20 during braiding. The larger diameter portion may include a flared portion, a stepped portion and the like. Further, the larger diameter portion may be disposed anywhere along the length of the mandrel 22. Moreover, the mandrel 22 may have multiple larger diameter portions, which may be the same or different.

The present invention, however, is not limited to the used of a dual sized or flared mandrel 22. For example, as depicted in FIG. 6, braiding mandrel 22' may be a substantially constant diameter mandrel, which is useful for braiding substantially constant diameter stents 24. The depicted shapes of the mandrels 22, 22' are non-limiting and other shaped mandrels may suitably be used, such as dual flared or flanged mandrel, tapered mandrels, and the like. Moreover, the raised mandrel projections 52, 56 need not be present along the whole braiding length and/or circumference of the braiding mandrel 22. Selected portion of the braiding mandrel 22 may be free or partially free of the raised mandrel projections 52, 56 depending on the characteristics of the stent 24 to be produced.

FIG. 7 is an exploded view of a portion of the mandrel 22 further depicting the raised mandrel projections 52, 56. The raised mandrel projections 52, 56 are arranged in a regular pattern over the mandrel 22 so that adjacent or juxtaposed raised mandrel projections 52, 56 form guides or channels 58 for receiving the stent filaments 20 during braiding. FIGS. 8-10 further detail the raised mandrel projections 52, 56 of the present invention. As depicted in FIG. 8 the raised mandrel projections 52, 56 are in the shape of a square or rectangular pyramid, having a square or rectangular base 60 and four triangular sides 62. As depicted in FIG. 9, the raised mandrel projections 52, 56 may have a truncated top portion 64. The top portion 64 may be somewhat rounded (not shown), if desired. Truncated and/or rounded top portions 64 are useful for easy removal of the stent 24 from the mandrel 22. For example, to remove the stent 24 from the mandrel 22 the stent 24 may be longitudinally compressed which causes the diameter of the stent 24 to increase. The stent filaments 20 may then clear over the truncated and/or rounded top portions 64, thereby releasing the stent 24 from the mandrel 22. Depending upon, for example, the braiding angle of the stent filaments 20 and/or the height of the raised mandrel projections 52, 56, the raised mandrel projections 52, 56 may be truncated to so form the truncated and/or rounded top portions 64 of the mandrel 22. Truncated and/or rounded top portions 64 may also be useful for guiding the stent filaments 20 into the guides or channels 58 of the mandrel 22. Further, as depicted in FIG. 10, the raised mandrel projections 52, 56 may further include a square or rectangular base portion 66 to further define the guides or channels 58 of the mandrel 22. Such features of the raised mandrel projections 52, 56 are useful for forming mandrel guides or channels 58 so that accurate placement of the stent filaments 20 is achieved during braiding, including accurate placement of the stent filaments 20 over dimensional variations of the mandrel 22, such as flared or tapered portions. The present invention, however, is not limited to the use square or rectangular pyramid shaped raised mandrel projections 52, 56, and other suitably shaped projection may suitably be used. For example, pins or projections, including removable pins or projections may suitably be used. The raised mandrel projections 52, 56 may be formed by cutting or etching away portion of the mandrel, such as by laser cutting, machine cutting, chemical etching, and the like. Further, the guides or channels 58 may be formed as grooves in the mandrel. Moreover, the raised mandrel projections 52, 56 forming the channels 58 may be on a collar or sleeve which may be releasably secured to the braiding mandrel itself.

Figure 12:
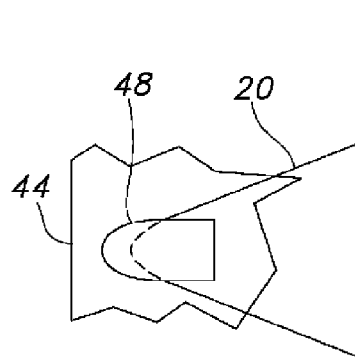
FIG. 12 is a top view of a raised projection of FIG. 11.
Figure 11:
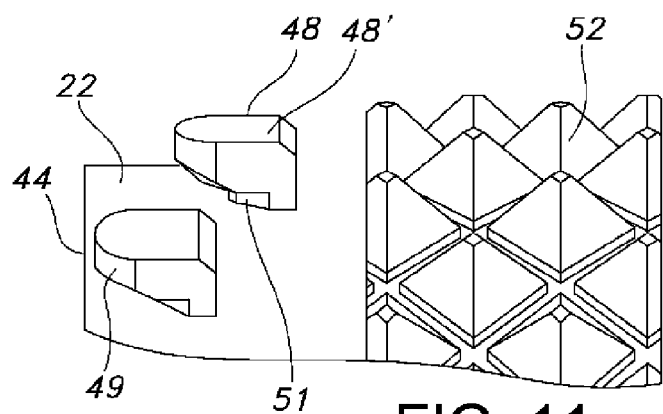
FIG. 11 is an exploded view of a portion of the distal end of the braiding mandrel of FIG. 5 or 6 depicting raised projection on the distal end.

FIG. 11 is an exploded view of a portion of the distal end 44 of the braiding mandrel 22. The securement projections 48 are depicted as being raised tabs 48'. The raised tabs 48' have a rounded face 49 for ease of securement of the stent filaments 20 and for safety by generally eliminating shape and pointed faces on the mandrel 22. As depicted in FIG. 12, the raised tab 48' is useful for bending a stent filament 22 about an under portion 51 of the raised tab 48'. The under portion 51 of the raised tab 48' is recessed from the rounded face 49 to secure the stent filament wire 20 thereat. Further, the under portion 51 of the raised tab 48' may be contoured so that the shape of the bend 36 of at the distal end 34 of the stent 24 corresponds to the shape of the under portion 51 of the raised tab 48'. The present invention, however, is not limited to such described under portion 51 of the raised tab 48' as securement projections 48, and as described below other configurations for the securement projections 48 may suitably be used. Moreover, the present invention is not limited to the securement of one stent filament 20 around one raised tab 48'. For example, if desired, two or more stent filaments 20, which may be the same or different including different material and/or specifications, may be secured about one raised tab 48' and then braided according to the techniques of the present invention.

Figure 13:
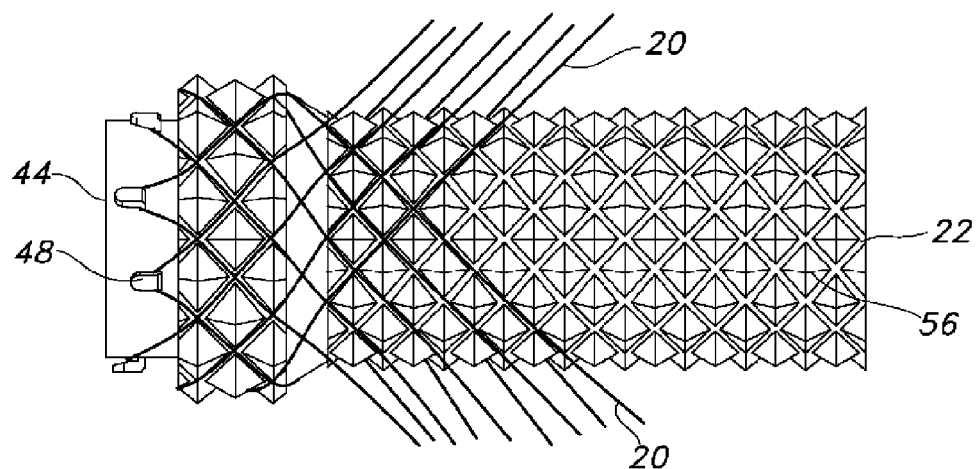
FIG. 13 depicts the braiding mandrel having middle portions of the stent filaments secured to the raised projections.
Figure 14:
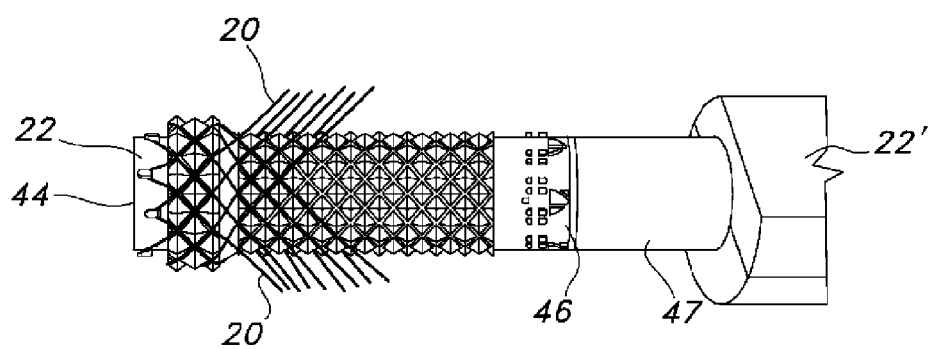
FIG. 14 depicts stent filaments being braided over the mandrel of the present invention.

FIG. 13 depicts the braiding mandrel 22 having middle portions of the stent filaments 20 secured to the raised projections 48'. Further, the stent filaments 20 are disposed within the channels 58 of the mandrel 22 formed between juxtaposed raised projections 52, 56. FIG. 14 depicts the stent filaments 22 being braided over the mandrel 20. Further, one end, for example the proximal end 46, of braiding mandrel 22 may be releasably secured to the mandrel 22' of the braiding machine 10 by a sleeve 47. Other arrangements may be suitably be used to secure the braiding mandrel 22 to the mandrel 22' of the braiding machine 10.

Figure 15:
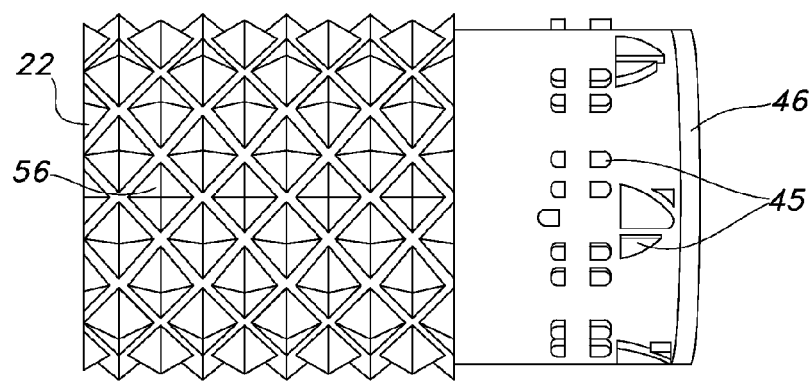
FIG. 15 is an exploded view of the proximal end of the braiding mandrel of the present invention.

FIG. 15 is an exploded view of the proximal end 46 of the braiding mandrel 22. The proximal end of the braiding mandrel 22 may include projections 45 which are useful for forming the closed loops 39 of stent 24. Such closed loops may be formed by bending the filaments 20 around the projections 45 (not shown). Details for forming such closed loops 39 may be found in U.S. Patent Application Publication Nos. 2005/0049682 A1 to Leanna et al.; 2005/0256563 A1 to Clerc et al.; and 2006/0116752 A1 to Norton et al., the contents of which are incorporated herein by reference.

The braiding mandrels 22 of FIGS. 5-15 are depicted as being useful for manufacturing a single stent. The braiding mandrels 22 of the present invention, however, are not so limited. For example, several stents 24 may be produced on a single mandrel 22 by providing different mandrel regions each having the securement projections 48 for commencing the braiding of a stent portion; channels 58 for receiving and controlling the stent filaments 20 within the particular section; and projections 45 for finishing the atraumatic stents 24 of the present invention. The several or multiple stents 24, i.e., two or more, may be the same or may have different stent configurations including stent diameters and stent lengths. In other words, the techniques and devices of the present invention allow for the manufacture of a highly customizable stent or highly customizable stents. Such customizable aspects of the stent may include but are not limited to the customization of stent lengths, stent diameters, stent curvatures, stent geometries, including atraumatic stent end geometries, and the like.

Figure 16A:
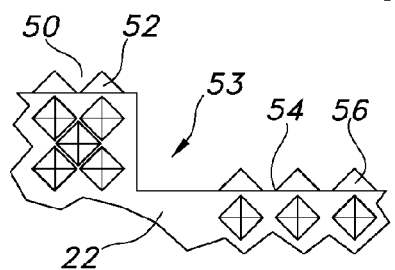
FIGS. 16A and 16B are partial exploded views of a transitional portion of the braiding mandrel of the present invention.
Figure 16B:
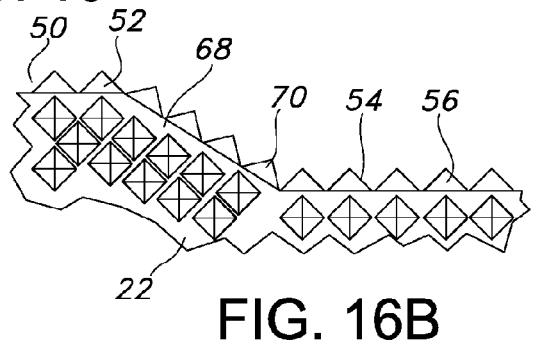

FIGS. 16A and 16B are partial exploded views of a portion of the braiding mandrel 22 of the present invention. As depicted in FIG. 16A, the distal mandrel portion 50 has a larger diameter than a diameter of the longitudinal mandrel portion 54. The transition 53 between the distal mandrel portion 50 and the longitudinal mandrel portion 54 is a simple step down in mandrel 22 diameters. As depicted in FIG. 16B, a transition region 68 is disposed between the larger distal portion 50 and the smaller the longitudinal mandrel portion 54. The transition region 68 is a sloped, desirably conical, region between the two diameters. The transition region 68 may further include raised mandrel projections 70, similar to the above-described shaped raised projections 52, 56.

Figure 17:
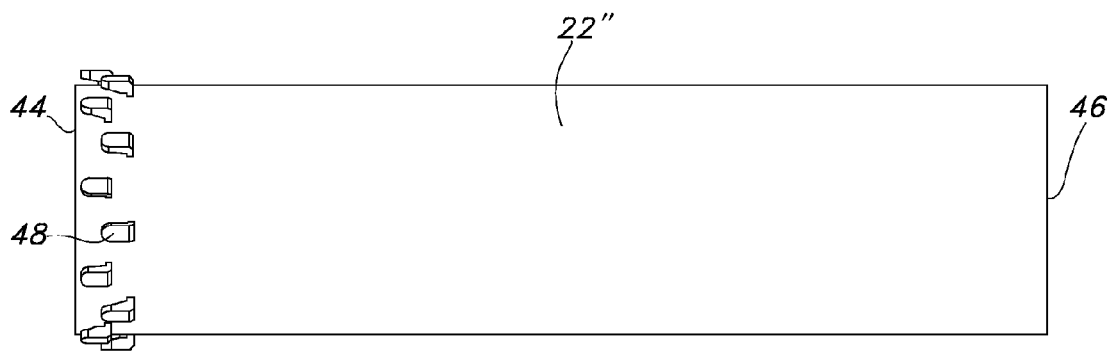
FIG. 17 depicts a braiding mandrel of the present which is free of the raised projections.

While aspects of the present invention have been described as using a mandrel 22, 22' having raised projections 52, 56 to provide, the present invention is not so limited. For example, as depicted in FIG. 17, where it is desirable, a braiding mandrel 22" which is free or substantially free of the above described raised projections 52, 56 may suitably be used. Such a mandrel 22" may still include the above described securement projections 48 at its distal end 44 and projections 45 (not shown) at its proximal end 46.

Figure 18:
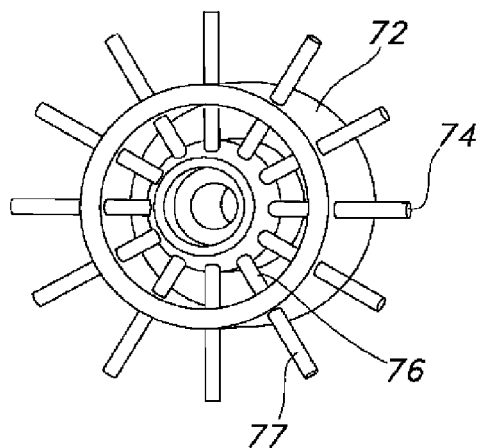
FIGS. 18-21 illustrate alternate embodiments for securing stent filaments at the distal end of the braiding mandrel.
Figure 19:
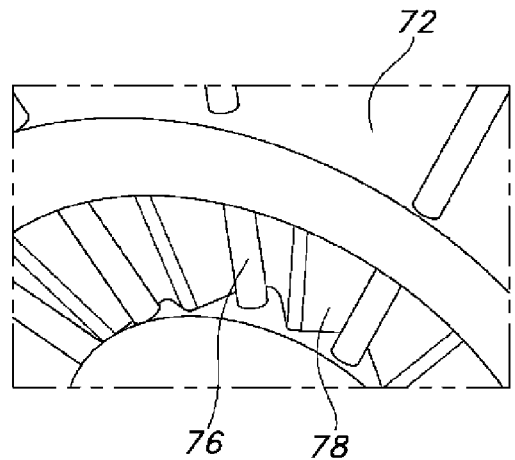

FIGS. 18-21 illustrate alternate embodiments of the securement projections 48 for securing stent filaments 20 at the distal end 44 of the braiding mandrel 22. These embodiments may be releasably secured to the distal end 44 of the braiding mandrel 22 or in some cases integrally formed with the distal end 44 of the braiding mandrel 22, such as but not limited to the above described raised tabs 48'. FIGS. 18-19 depict a wagon wheel arrangement 72 for securing stent filaments 20 at the distal end 44 of the braiding mandrel 22. The wagon wheel 72 may include pins 74 around which the stent filaments 20 may be disposed. The stent filaments 20 may be disposed about the inner portions 76 of the pins 74, but if desired the stent filaments 20 may be disposed outer pin portion 77. The wagon wheel 72 may further include an undulating surface 78. The undulating surface 78 is useful in positioning the stent filaments 20 within the wagon wheel 72. Further, the shape of the undulating surface 78 may be altered to conform to the desired angle of the bends 36 of the stent 24.

Figure 20:
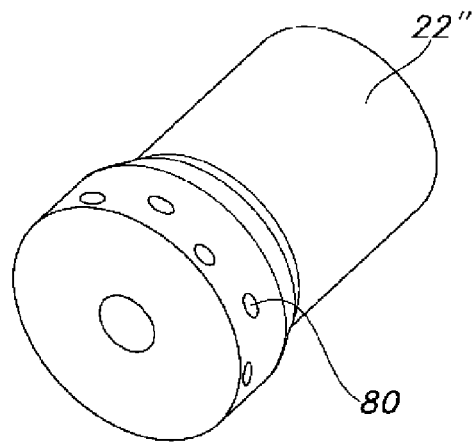
Figure 21:
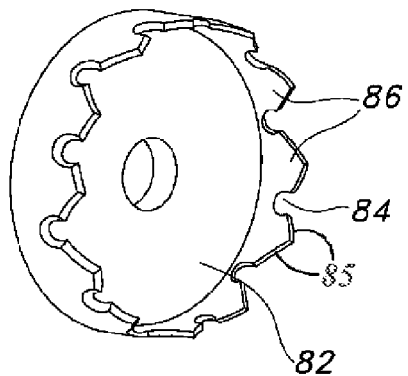

FIG. 20 depicts a mandrel 22" having holes 80 at its distal end. Screws, pins, tabs, detents and the like (not shown) may be inserted into the holes 80 for securing stent filaments 20 (not shown) thereat. As depicted in FIG. 21, a cap 82 may be used in conjunction with the embodiment of FIG. 20. The cap 82 may have a plurality of semicircular notches 84 which receive the pins or screws described in conjunction with FIG. 20. The cap 82 may further include projections 86 with angular or sloped surfaces 85 which are useful for setting and orientation, configuration and/or angle of the bends 36 of the stent 24. While this embodiment of the projections for securing the stent filaments 20 is shown as being integrally formed into the mandrel 22", the holes 80 may be integrally formed in any of the other described mandrels 22, 22', or may be formed as a separate device which may be releasably secured to any of the braiding mandrels 22, 22', 22".

Figure 22:
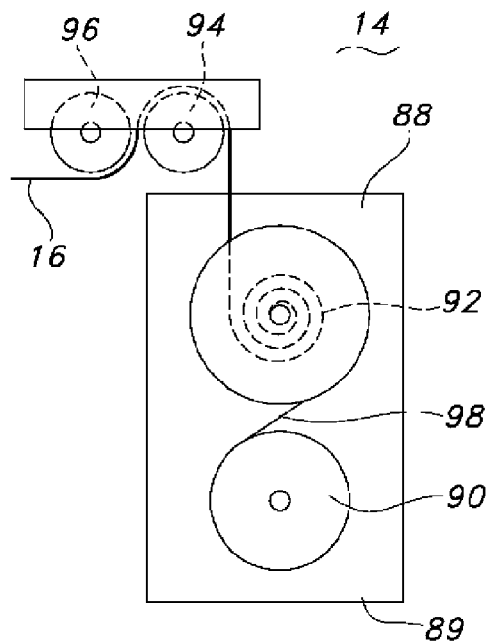
FIG. 22 is a schematic depiction of a constant force carrier of the present invention.

FIG. 22 is a schematic depiction of a tensioned or constant force braiding carrier 14 of the present invention. The constant force carrier 14 may include a frame 88 for holding wheels 90, 92, 94, 96 and spring 98. The retractable carrier filament 16 may have one end securably wound around wheel 92. The retractable carrier filament 16 may exit the constant force carrier 14 via wheels 94, 96, as shown. The wheels 94, 96 are useful in guiding the retractable carrier filament 16 toward the braiding zone 32. Spring 98 generally imparts a constant force from wheel 90 to wheel 92 to provide, in part, a constant tension to the retractable carrier filament 16. The retractable carrier filament 16 may itself coil or wrap around wheel 92 to be in communication with the tension applied by the spring 98. Further, as the stent 24 is being braided, the retractable carrier filament 16 may uncoil or unwrap from the wheel 92 to accommodate the movement of the stent filaments 20 within the braiding zone 32. The bottom portion 89 of the frame 88 of constant force carrier 14 may be releasably secured to the notch gear 14 as schematically depicted in FIGS. 1-2. The constant force carrier 14 of FIG. 22 does not include a bobbin having stent forming filaments 20 wound thereon. In other words the constant force carrier 14 of FIG. 22 includes the retractable carrier filament 16 to the exclusion of the stent forming filament 20.

The constant force or tensioned braiding carrier 14 is useful for braiding discrete lengths of stent forming filaments 20. With the use of the constant force or tensioned braiding carriers 14, all or substantially all of the stent forming filaments 20 are disposed directly within the braiding zone 32. Thus, constant tension or substantially constant tension on the stent forming filaments 20 is controlled and maintained directly within the braiding zone 32. Braiding techniques of the prior art do not have such direct control of filament tension within the braiding zone, leading to possible greater variation of braiding angles and stent cell sizes.

Figure 23:
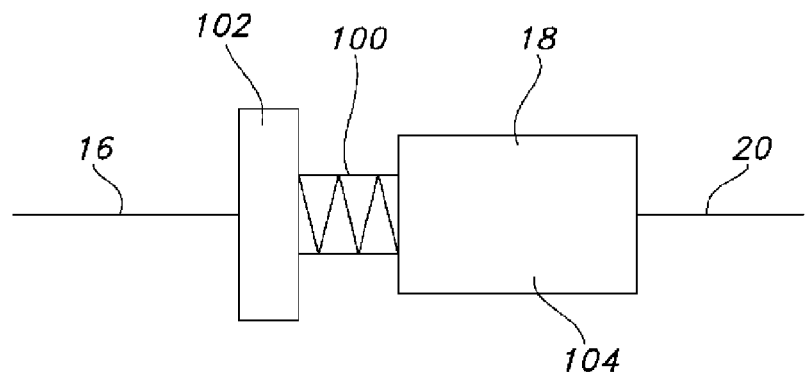
FIG. 23 is a schematic of a clip mentioned in FIG. 1.

FIG. 23 is a schematic of one embodiment of the clip 18 described above in conjunction with FIG. 1. The clip 18 is depicted as a quick release clip, but any clip or securing mechanism may suitably be used to secure the stent forming filament 20 to the retractable carrier filament 16. The retractable carrier filament 16 may be securably disposed to releasably secure to the clip 18. The stent forming filament 20 is desirably releasably secured to the clip 18. A spring 100 may be used between a knob 102 and a body 104 of the clip 18. Moving the knob 102 toward the clip body 104, which is against the force of the spring 100, releases the stent forming element 20 from the clip 18 by moving filament engaging portions (not shown) within the body 104 of the clip 18.

Figure 24:
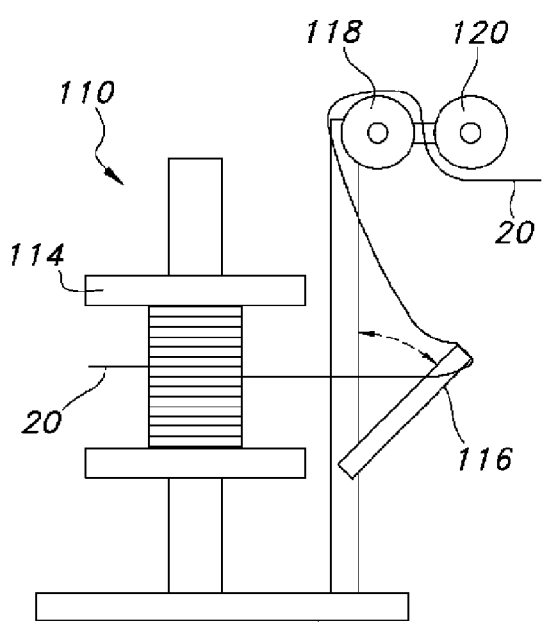
FIG. 24 is a schematic of an alternate embodiment of a constant force bobbin carrier of the present invention.

FIG. 24 schematically depicts an alternate embodiment of a constant force bobbin carrier 110 which may be used in accordance with the present invention. The constant force bobbin carrier 110 includes a bobbin 114 upon which the stent forming filament 20 is wound. The constant force bobbin carrier 110 includes a latch spring 116 which provides constant tension to the stent forming filament 20. The latch spring 116 typically includes an eyelet (not shown) or a small wheel to guide the stent forming filament 20. The latch spring 116 is typically moveable away from the bobbin 114, as indicated by the vector, to provide tension to the stent forming filament 20. The stent forming filament 20 then travels about a first wheel 118 and a second wheel 120. The stent forming wire 20 exits the constant force bobbin carrier 110 toward the braiding zone 32 for braiding the stent 24 in accordance with the present invention. Typically, the stent forming filament 20 is partially unwound from one bobbin 114 and then the unwound portion is rewound onto another bobbin 114 of another the constant force bobbin carrier 110 (not shown). After the constant force bobbin carriers 110 are secured to the notch gears 12, the middle portion of the stent forming filament 20 may be then engaged to the securement projections 48 of the braiding mandrel 22 to braid the stent in accordance with the present invention. This alternative embodiment may be, however, more time consuming as the stent filaments must be rewound onto bobbins 114.

Use of the constant force bobbin carriers 110 in conjunction with the braiding mandrels 22, 22' having distal securement projections 48 and braiding channels 58 provide for suitable tension control to braid the stents of the present invention. The constant force braiding carriers 110, however, may require greater lengths of filaments 20 as compared to the use of the tensioned braiding carriers 14. As such, greater portions of the filaments 20 may be outside the braiding zone 32 with the use of the bobbin carriers 110, which may lead to less direct control of the tension on the filaments 20 within the braiding zone 32.

In yet an alternate embodiment, a combination of constant force carriers 14 and constant force bobbin carriers 110 may be used where instead of rewinding the stent filament 20 onto another bobbin 114 the stent filament end exiting the bobbin 114 may be releasably secured to a constant force carrier 14 via the clip 18.

Desirably, the constant force carriers 14 and the constant force bobbin carrier 110, in conjunction with the other embodiments of the present invention, are configured and controlled to provide a controlled tension to the filaments 16, 20 during braiding of the stent 24 over mandrel 22. Useful tension forces include substantially constant tensile forces from about ⅛ or 0.125 pound-force (about 0.5 Newtons) to about 10 pound-force (about 45 Newtons). Desirably, the tensile force is from about ¼ or 0.25 pound-force (about 1 Newton) to about 10 pound-force (about 22 Newtons). Preferably, the tensile force is from about ½ or 0.5 pound-force (about 2 Newtons) to about 3 pound-force (about 13 Newtons). In general, the larger the diameter of the filament 20 the larger tensile force will be applied. Minimum force levels are necessary to securely hold the filaments 20 on the mandrel 22 during braiding and subsequent processing steps. If too much force is applied, then the filaments 20 may stretch or deform on the mandrel 22, in particular if the stent is heat treated while on the mandrel 22, which is referred to as necking of filaments or wires. Such necking is undesirable as it may weaken the filament or wire and possibly leading toward fracture of the filament or wire. These above-described tensile forces are desirably useful for braiding metallic filaments 20. When non-metallic, for example polymeric, filaments 20 are braided to form the stent 24, the tension force applied may be less than the values for metallic filaments 20. For example, a tensile force from about 0.5 pound-force (about 2 Newton) to about 1 pound-force (about 2 Newtons) is useful for braiding polymeric filaments 20.

Figure 25:
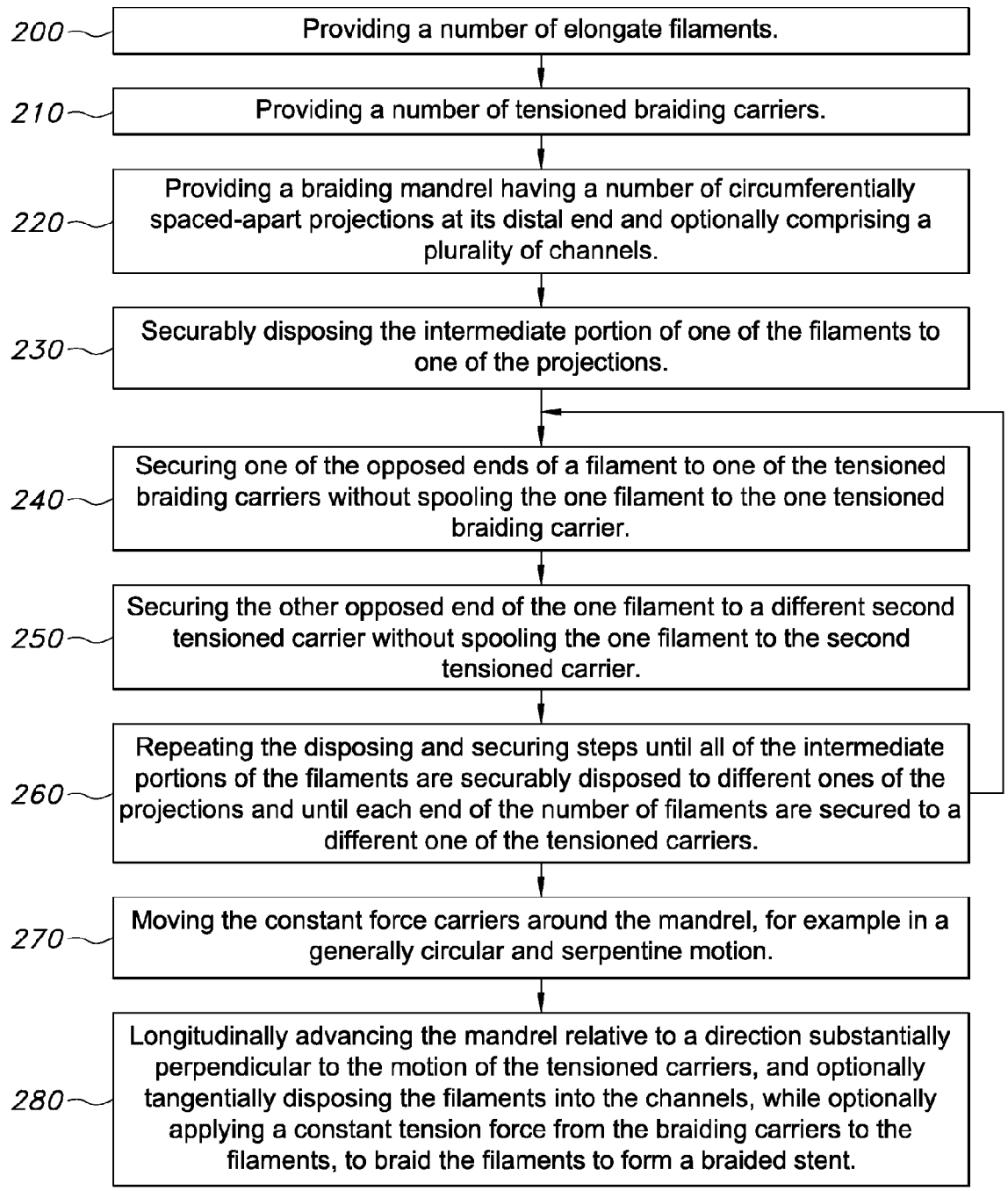
FIG. 25 is a schematic of a method of forming the stent of the present invention.

FIG. 25 depicts a method for braiding the stent 24 of the present invention. At step 200, a number of elongate stent filaments are provided. Each of the filaments has opposed ends and an intermediate portion between the opposed ends. At step 210, a number of tensioned braiding carriers is provided. At step 220, a braiding mandrel having opposed proximal and distal ends is provided. The braiding mandrel may include a number of circumferentially spaced-apart securement projections at the distal end of the braiding mandrel and may optionally include a plurality of grooves or channels for receiving the stent filaments during braiding. At step 230, the intermediate portion of one of the filaments is securably disposed to one of the securement projections. At step 240, one of the opposed ends of the one filament is secured to one of the tensioned braiding carriers without spooling the one filament to the one tensioned braiding carrier. At step 250, the other opposed end of the one filament is secured to a different second tensioned carrier without spooling the one filament to the second tensioned carrier. At step 260, steps 230-250 are repeated until all of the intermediate portions of the filaments are securably disposed to different ones of the securement projections and until each end of the number of filaments are secured to a different one of the tensioned carriers. At step 270, the tensioned carriers are moved in a generally circular and serpentine motion. At step 280, the mandrel is longitudinally advanced relative to a direction substantially perpendicular to the motion of the tensioned carriers to braid the filaments to form a braided stent.

The method of this embodiment may further include the step of applying a constant tension from the tensioned braiding carriers to the filaments, wherein the constant tension force is form about 0.25 pound-force (1.1 Newtons) to about 5 pound-force (22.2 Newtons). Further, the number of securement projections may be about one-half the number of filaments, but any suitable number of securement projections may be used. The number of tensioned carriers may be about twice the number of filaments, but any suitable number of tensioned carriers may be used. Desirably, the number of filaments may be from about 6 to about 40 or more. Such numbers of securement projections and tensioned carriers are non-limited, and any suitable relative numbers of securement projections and tensioned carriers may be used. For example, the number and type of filaments 20 may be increased and/or decreased during braiding stent, including braiding different sections of stents with different types of material and/or different number of filaments.

The mandrel may include a plurality of grooves or channels and further where the filaments are disposed into the grooves during the braiding of steps 270 through 280. The filaments may be tangentially disposed within the grooves during the braiding steps 270 through 280. Desirably, the steps 270 through 280 are continued until the filaments are braided to a portion of the mandrel near the proximal end of the mandrel. The braiding method may further include the step of securing the filaments to the portion of the mandrel while maintaining the filaments under a tension force from about 0.25 pound-force (1.1 Newtons) to about 5 pound-force (22.2 Newtons). Further, the stent may be heat treated. Desirably, the heat treating of the stent filaments may be performed while the filaments are disposed on the mandrel and also while the filaments are under the tension force.

The securement projections at the distal end of the braiding mandrel may be selected from hooks, pins, tabs, screws and combinations thereof. The securement projections may be removable from the mandrel. The distal end of the braiding material may further include a collar having the securement projections disposed thereto.

Further, the mandrel may include a first portion having a first diameter, and a second portion having a second diameter, where the first diameter is different from the second diameter. The mandrel may include a plurality of portions having different diameters. Moreover, the mandrel may include interchangeable portions which may be connectable along the length of the mandrel or even along the circumference of the mandrel, or combinations thereof. Grooves may be disposed throughout the first and second portions. Further, a constant tension force may be applied from the constant force braiding carriers to the filaments so that a braiding angle between intersecting braided filaments is substantially equal in the first and second portions. The mandrel may further include a transition portion between the first and second portions. Desirably, the braiding angle is substantially equal in the first portion, the transition portion and the second portion. The present invention, however, is not so limited, and the braiding angles may be controlled to any custom values, including controlled variation of the braiding angle over straight stent section and non-straight stent sections, such as flared sections, flanged sections, curved sections and the like.

The filaments may be selected from metallic filaments, polymeric filaments, and combinations thereof. The filaments may be single strand or multi-strand filaments. The strands of the multi-strand filaments may be the same or different, such as but not limited to different materials, different geometries, different mechanical properties, different physical properties, different chemical properties, and the like. Desirably, the filaments are metallic filaments, including nitinol filaments or nitinol-containing filaments.

Figure 26:
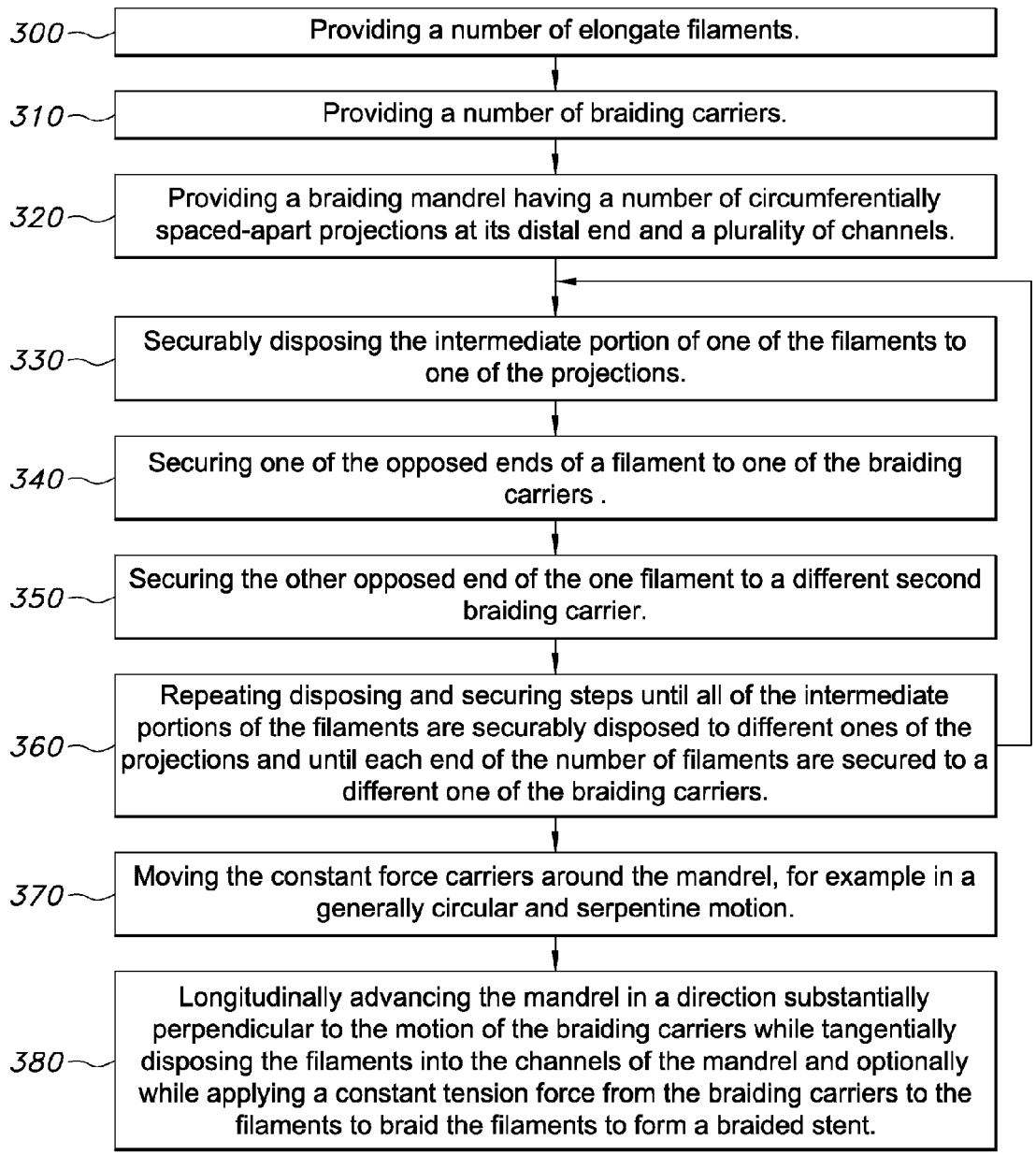
FIG. 26 is a schematic of another method of forming the stent of the present invention.

FIG. 26 depicts another embodiment of a method for braiding the stent 24 of the present invention. At step 300, a number of elongate filaments are provided with each of the filaments having opposed ends and an intermediate portion between the opposed ends. At step 310, a number of braiding carriers are provided. At step 320, a braiding mandrel having opposed proximal and distal ends is provided. The braiding mandrel may include a number of circumferentially spaced-apart securement projections at the distal end and may optionally further include a plurality of grooves. At step 330, the intermediate portion of one of the filaments is securably disposed to one of the securement projections at the distal end of the mandrel. At step 340, one of the opposed ends of the one filament is secured to one of the braiding carriers. At step 350, the other opposed end of the one filament is secured to a different second braiding carrier. At step 360, steps 330 through 350 are repeated until all of the intermediate portions of the filaments are securably disposed to different ones of the securement projections and until each end of the number of filaments are secured to a different one of the braiding carriers. At step 370, the braiding carriers are moved in a generally circular and serpentine motion. At step 380, the mandrel is longitudinally advanced relative to the braiding machine in a direction substantially perpendicular to the motion of the braiding carriers to braid the filaments to form a braided stent; and optionally a constant tension force, for example from about 0.25 pound-force (1.1 Newtons) to about 5 pound-force (22.2 Newtons), is applied from the braiding barriers to the filaments during the braiding of the filaments.

The braiding carriers of this embodiment may be constant force carriers. The ends of the filaments may be securably disposed to the constant force carriers without spooling the filaments to the constant force carriers. Alternatively or in addition to, some or all of the braiding carriers may include a bobbin where a portion of the filament is spooled about the bobbin.

While the invention has been described through the use of a braiding machine, certain aspects of the present invention may also be useful with hand braiding or hand weaving method to form a stent. In such a case the braiding mandrel may further include additional tabs, pins or the like along its longitudinal length about which a tension of the braiding filaments may be obtained.

The stent 24 of the present invention may include a therapeutic agent in a coating. The therapeutic agent in a coating of the stent 24 of the present invention may be any suitable biologically acceptable agent such as a non-genetic therapeutic agent, a biomolecule, a small molecule, or cells.

Exemplary non-genetic therapeutic agents include anti-thrombogenic agents such as heparin, heparin derivatives, prostaglandin (including micellar prostaglandin E1), urokinase, and PPack (dextrophenylalanine proline arginine chloromethyl ketone); anti-proliferative agents such as enoxaparin, angiopeptin, sirolimus (rapamycin), tacrolimus, everolimus, zotarolimus, biolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc-oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamicin, rifampin, minocycline, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds including anti-thrombin antibodies, platelet receptor antagonists, anti-platelet receptor antibodies, enoxaparin, hirudin, warfarin sodium, dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include SERCA 2 protein, monocyte chemoattractant proteins ("MCP-1") and bone morphogenic proteins ("BMPs"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathepsin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds that have a molecular weight of less than 100 kD.

Exemplary cells include stem cells, progenitor cells, endothelial cells, adult cardiomyocytes, and smooth muscle cells. Cells can be of human origin (autologous or allogeneic) or from an animal source (xenogeneic), or genetically engineered. Non-limiting examples of cells include side population (SP) cells, lineage negative (Lin$^-$) cells including Lin$^-$CD34$^-$, Lin$^-$CD34$^+$, Lin$^-$c Kit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, G$_0$ cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the stent 24 or applied onto a polymeric coating on the stent 24. The polymers of the polymeric coatings may be biodegradable or non-biodegradable. Non-limiting examples of suitable non-biodegradable polymers include polystyrene; polystyrene maleic anhydride; polyisobutylene copolymers such as styrene-isobutylene-styrene block copolymers (SIBS) and styrene-ethylene/butylene-styrene (SEBS) block copolymers; polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides including poly(methylmethacrylate-butylacetate-methylmethacrylate) block copolymers; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropyl methyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The stent 24 may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

The stent 24 are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like. Further, the stent 24 may contain any of the above described polymer coatings with or without any of the above described therapeutic agents. Moreover, only portions, such as but not limited to portions of the stent 24 disposed between stent ends 34, 38 or even just portions of one or both stent ends 24, 38, may contain any of the above described polymer coatings with or without any of the above described therapeutic agents.

The embodiments or aspects of the invention, including the embodiments presented in the claims, may be combined in any fashion and combination and be within the scope of the present invention. As a nonlimiting example, the following embodiments or aspects of the invention may be combined in any fashion and combination and be within the scope of the present invention, as follows:

Embodiment 1

A method of braiding a stent comprising: (a) providing a number of elongate filaments, each of the filaments having opposed ends and an intermediate portion between the opposed ends; (b) providing a number of tensioned braiding carriers; (c) providing a braiding mandrel having opposed proximal and distal ends, the braiding mandrel comprising a number of circumferentially spaced-apart securement projections at the distal end of the braiding mandrel; (d) securably disposing the intermediate portion of one of the filaments to one of the securement projections; (e) securing one of the opposed ends of the one filament to one of the tensioned braiding carriers; (f) securing the other opposed end of the one filament to a different second tensioned braiding carrier; (g) repeating steps (d) through (f) until all of the intermediate portions of the filaments are securably disposed to different ones of the securement projections and until each end of the number of filaments are secured to a different one of the tensioned braiding carriers; (h) moving the tensioned braiding carriers around the mandrel; and (i) longitudinally advancing the mandrel in a direction substantially perpendicular to the motion of the tensioned braiding carriers to braid the filaments to form a braided stent.

Embodiment 2

The method of embodiment 1, wherein step (h) includes moving the tensioned braiding carriers in a generally circular and serpentine motion about a circumferential plane of the mandrel.

Embodiment 3

The method of embodiment 1, wherein the tensioned braiding carriers each comprise a retractable carrier filament and further wherein step (e) includes securing the one opposed end of the one filament to the retractable carrier filament of the one tensioned braiding carrier and step (f) includes securing the other opposed end of the one filament to the retractable carrier filament of the second tensioned braiding carrier.

Embodiment 4

The method of embodiment 2, wherein the tensioned braiding carriers each comprise a wheel and wherein the retractable carrier filament of the tensioned braiding carrier is coiled about the wheel.

Embodiment 5

The method of embodiment 1, further comprising: applying a constant tension from the tensioned braiding carriers to the filaments, wherein the constant tension force is form about 0.25 pound-force to about 5 pound-force.

Embodiment 6

The method of embodiment 1, wherein the number of securement projections is about one-half the number of filaments.

Embodiment 7

The method of embodiment 1, wherein the number of tensioned braiding carriers is about twice the number of filaments.

Embodiment 8

The method of embodiment 1, wherein the number of filaments is from about 6 or more.

Embodiment 9

The method of embodiment 1, wherein the mandrel comprises a plurality of grooves and further wherein the filaments are disposed into the grooves during the braiding of steps (h) through (i).

Embodiment 10

The method of embodiment 9, wherein the filaments are tangentially disposed on the mandrel within the grooves during the braiding steps (h) through (i).

Embodiment 11

The method of embodiment 1, wherein the securement projections at the distal end of the braiding mandrel are selected from the group consisting of hooks, pins, tabs, screws and combinations thereof.

Embodiment 12

The method of embodiment 1, wherein the securement projections the distal end of the braiding mandrel are removable from the mandrel.

Embodiment 13

The method of embodiment 1, wherein the distal end of the braiding material further comprises a collar having the securement projections disposed thereto, and further wherein the securement projections are selected from the group consisting of hooks, pins, tabs, screws and combinations thereof.

Embodiment 14

The method of embodiment 9, wherein steps (h) through (i) are continued until the filaments are braided to a portion of the mandrel near the proximal end of the mandrel, and further comprising the step of securing the filaments to the portion of the mandrel while maintaining the filaments under a tension force from about 0.25 pound-force to about 5 pound-force.

Embodiment 15

The method of embodiment 14, further comprising heat treating the filaments while the filaments are disposed on the mandrel.

Embodiment 16

The method of embodiment 9, wherein the mandrel comprises a first portion having a first diameter, and a second portion having a second diameter, wherein the first diameter is different from the second diameter, and wherein the grooves are disposed throughout said first and second portion, and further comprising the step of applying a tension force from the constant force braiding carriers to the filaments so that a braiding angle between intersecting braided filaments is substantially equal in the first and second portions.

Embodiment 17

The method of embodiment 16, wherein the mandrel further comprises a transition portion between the first and second portions and further wherein the braiding angle is substantially equal in the first portion, the transition portion and the second portion.

Embodiment 18

The method of embodiment 1, wherein the filaments are selected from the group of metallic filaments, polymeric filaments, and combinations thereof.

Embodiment 19

The method of embodiment 1, wherein the filaments are metallic filaments comprise nitinol.

Embodiment 20

A method for braiding a stent comprising: (a) providing a number of elongate filaments, each of the filaments having opposed ends and an intermediate portion between the opposed ends; (b) providing a number of braiding carriers; (c) providing a braiding mandrel having opposed proximal and distal ends, the braiding mandrel comprising a number of circumferentially spaced-apart securement projections at the distal end, the mandrel further comprising a plurality of grooves; (d) securably disposing the intermediate portion of one of the filaments to one of the securement projections at the distal end of the mandrel; (e) securing one of the opposed ends of the one filament to one of the braiding carriers; (f) securing the other opposed end of the one filament to a different second braiding carrier; (g) repeating steps (d) through (f) until all of the intermediate portions of the filaments are securably disposed to different ones of the securement projections and until each end of the number of filaments are secured to a different one of the braiding carriers; (h) moving the braiding carriers around the mandrel; (i) longitudinally advancing the mandrel relative to a direction substantially perpendicular to the motion of the braiding carriers to braid the filaments to form a braided stent; and (j) applying a constant tension force from the braiding barriers to the filaments during the braiding steps (h) through (i).

Embodiment 21

The method of embodiment 20, wherein step (h) includes moving the braiding carriers in a generally circular and serpentine motion about a circumferential plane of the mandrel.

Embodiment 22

The method of embodiment 20, wherein the braiding carriers are constant force carriers and further wherein the ends of the filaments are securably disposed to the constant force carriers without spooling the filaments to the constant force carriers.

Embodiment 23

The method of embodiment 20, wherein the braiding carriers comprise a bobbin and wherein a portion of the filament is spooled about the bobbin.

Embodiment 24

The method of embodiment 20, wherein the constant tension force is from about 0.25 pound-force to about 5 pound-force.

Embodiment 25

A method for braiding a stent comprising: (a) providing a number of elongate filaments, each of the filaments having opposed ends and an intermediate portion between the opposed ends; (b) providing a number of tensioned braiding carriers; (c) providing a braiding mandrel having opposed proximal and distal ends, the braiding mandrel comprising a number of circumferentially spaced-apart securement projections at the distal end, the braiding mandrel further comprising a plurality of grooves; (d) securably disposing the intermediate portion of one of the filaments to one of the securement projections at the distal end of the braiding mandrel; (e) securing one of the opposed ends of the one filament to one of the tensioned braiding carriers without spooling the one filament to the one tensioned braiding carrier; (f) securing the other opposed end of the one filament to a different second tensioned carrier without spooling the one filament to the second tensioned carrier; (g) repeating steps (d) through (f) until all of the intermediate portions of the filaments are securably disposed to different ones of the securement projections and until each end of the number of filaments are secured to a different one of the tensioned carriers; (h) moving the tensioned carriers around the mandrel; and (i) longitudinally advancing the mandrel relative to a direction substantially perpendicular to the motion of the tensioned carriers to braid the filaments by tangentially disposing the filaments into the grooves to braid the filaments to form a braided stent.

Embodiment 26

The method of embodiment 25, wherein step (h) includes moving the braiding carriers in a generally circular and serpentine motion about a circumferential plane of the mandrel.

Embodiment 27

The method of embodiment 25, further comprising applying a constant tension force is from about 0.25 pound-force to about 5 pound-force.

Embodiment 28

A braided stent comprising: a plurality of elongate filaments inter-braided to form a tubular well structure, the filaments being inter-braided at a braiding angle formed at crossing filament locations; the tubular wall structure comprising a first portion having a first diameter, a second portion having a second diameter which is different from the second diameter and a transition portion disposed between the first portion and the second portion; wherein the braiding angles in the first portion are substantially equal, wherein the braiding angles in the second portion are substantially equal, and wherein the braiding angles in the transition portion are substantially equal.

Embodiment 29

The braided stent of embodiment 28, wherein the braiding angles in the first portion, wherein the braiding angles in the second portion and wherein the braiding angles in the transition portion are substantially equal.

Embodiment 30

The braided stent of embodiment 29, wherein the braiding angles in the first portion, the second portion and the transition portion are all within 5 degrees of one and the other.

Embodiment 31

The braided stent of embodiment 29, wherein the braiding angles in the first portion, the second portion and the transition portion are all within 1 degree of one and the other.

Embodiment 32

The braided stent of embodiment 29, wherein the braiding angle is an obtuse angle between longitudinally extending inter-braided filaments.

Embodiment 33

The braided stent of embodiment 28, wherein at least one of the braiding angles in the first portion, in the second portion or in the transition portion are different from the braiding angles from the other portions.

Embodiment 34

The braided stent of embodiment 28, wherein the filaments are selected from the group consisting of metallic filaments, polymeric filaments and combinations thereof.

Embodiment 35

The braided stent of embodiment 28, wherein the filaments are metallic filaments comprising nitinol.

Embodiment 36

A braiding mandrel for braiding a tubular stent comprising: an elongate tubular member having opposed proximal and distal ends; securement projections circumferentially disposed at spaced-apart locations at the distal end for engaging a filament from a braiding machine; a plurality of angularly disposed grooves along the longitudinal length of the member.

Embodiment 37

The braiding mandrel of embodiment 36, wherein the angularly disposed grooves extend at an angle from about 5.degree. to about 85.degree. from a longitudinal axis of the member.

Embodiment 38

The braiding mandrel of embodiment 36, further comprising: a plurality of spaced-apart projections wherein spaces between the projections define the plurality of angularly disposed grooves in the elongate member.

Embodiment 39

The braiding mandrel of embodiment 36, wherein the securement projections are selected from the group consisting of hooks, pins, tabs, screws and combinations thereof.

Embodiment 40

The braiding mandrel of embodiment 36 further comprising a collar disposed at the distal end of the tubular member, wherein the securement projections are disposed on the collar.

Embodiment 41

The braiding mandrel of embodiment 36, wherein the tubular member is a metallic member.

Embodiment 42

The braiding mandrel of embodiment 36, wherein the tubular member has a substantially constant diameter.

Embodiment 43

The braiding mandrel of embodiment 36, wherein the tubular member as a varied diameter.

Embodiment 44

The method of embodiment 1, wherein step (e) is performed without spooling the one filament to the one tensioned braiding carrier and step (f) is performed without spooling the one filament to the second tensioned braiding carrier.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

The invention claimed is:

1. A method of making a stent comprising:
   looping filaments around a plurality of securement projections of a mandrel, the plurality of securement projections being longitudinally staggered and circumferentially spaced; and
   braiding the filaments to form a stent with longitudinally staggered loops at a first end and closed loops at a second end of the stent.

2. The method of claim 1, wherein each securement projection has a single filament looped therearound.

3. The method of claim 1, each filament having an intermediate portion and opposed ends, wherein the intermediate portion is looped around the securement projection and the opposed ends are secured to a braiding machine.

4. The method of claim 1, the mandrel further defines first parallel helical pathways and second parallel helical pathways that intersect the first parallel helical pathways,
   wherein during the step of braiding the filaments, a filament is laid in each helical pathway.

5. The method of claim 4, the mandrel having raised projections that define the first parallel helical pathways and the second parallel helical pathways,
   wherein during the step of braiding the filaments, the raised projections provide for a substantially constant braiding angle for the filaments.

6. The method of claim 5, the raised projections having a different shape than a shape of the securement projections.

7. The method of claim 1, the mandrel further comprising raised projections aligned in a plurality bands, the plurality of bands including circumferential bands and longitudinal bands, wherein the raised projections in each circumferential band are circumferentially offset from the raised projections of at least one other circumferential band, and the raised projections in each longitudinal band are longitudinally offset form the raised projections of at least one other longitudinal band.

8. A method of making a stent comprising:
   looping filaments around securement projections secured to a mandrel; and
   braiding the filaments at a substantially constant braiding angle to form a stent with a loops at a first end; and
   forming loops at a second end of the stent.

9. The method of claim 8, wherein raised projections are secured to the mandrel, the raised projections being aligned in a plurality bands, the plurality of bands including circumferential bands and longitudinal bands, wherein the raised projections in each circumferential band are circumferentially offset from the raised projections of at least one other circumferential band, and the raised projections in each longitudinal band are longitudinally offset form the raised projections of at least one other longitudinal band, wherein during the step of braiding the filaments are laid in the channels.

10. The method of claim 9, wherein the raised projections provide for one substantially constant braiding angle.

11. The method of claim 9, wherein a first portion of the mandrel has a first diameter and a second portion of the mandrel has a second diameter different than the first diameter.

12. The method of claim 9, wherein a sleeve includes the raised projections and the sleeve is releaseably secured to the mandrel.

13. A method of making a stent comprising:
   providing filaments;
   forming first loops from the filaments;
   forming second loops from the filaments; and
   forming filament crossings from the filaments, the filament crossings being positioned between the first and second loops, each filament crossing having an angle, the angle being substantially constant for all of the filament crossings.

14. The method of claim 13, wherein the step of forming the filament crossings includes laying the filaments in a plurality of channels defined by raised projections secured to a mandrel, each filament crossing formed at a crossing of two of the plurality of channels.

15. The method of claim 14, wherein the raised projections are aligned in a plurality bands, the plurality of bands including circumferential bands and longitudinal bands, wherein the raised projections in each circumferential band are circumferentially offset from the raised projections of at least one other circumferential band, and the raised projections in each longitudinal band are longitudinally offset form the raised projections of at least one other longitudinal band.

16. The method of claim 14, wherein the step of forming first loops includes looping the filaments around circumferentially spaced securement projections that are secured to a first end region of the mandrel.

17. The method of claim 16, wherein the step of forming second loops includes bending the filaments around circumferentially spaced projections that are secured to a second end region of the mandrel.

18. The method of claim 13, wherein the stent includes portions of different diameters.

19. The method of claim 1, wherein the stent includes a first portion and a second portion, wherein the first portion has a different diameter than the second portion, and a braiding angle of the filaments in the first portion is different than a braiding angle of the filaments in the second portion.

20. The method of claim 1, wherein a braiding angle at one end of the stent is different from a braiding angle at an opposed second end of the stent.

* * * * *